(12) United States Patent
Alexandre et al.

(10) Patent No.: US 6,964,650 B2
(45) Date of Patent: Nov. 15, 2005

(54) NEEDLELESS SAFETY SYRINGE OF COMPACT ARCHITECTURE

(75) Inventors: Patrick Alexandre, Gray (FR);
Bernard Brouquieres, Toulon (FR);
Philippe Gautier, Le Plessis Pate (FR);
Marc Piel, Paris (FR)

(73) Assignee: Crossject, Paris (FR)

( * ) Notice: Subject to any disclaimer, the term of this patent is extended or adjusted under 35 U.S.C. 154(b) by 184 days.

(21) Appl. No.: 10/398,768

(22) PCT Filed: Oct. 19, 2001

(86) PCT No.: PCT/FR01/03237

§ 371 (c)(1),
(2), (4) Date: Apr. 15, 2003

(87) PCT Pub. No.: WO02/34317

PCT Pub. Date: May 2, 2002

(65) Prior Publication Data

US 2004/0015125 A1 Jan. 22, 2004

(30) Foreign Application Priority Data

Oct. 23, 2000 (FR) .................................. 00 13544

(51) Int. Cl.$^7$ .............................................. A61M 5/30
(52) U.S. Cl. ...................................................... 604/70
(58) Field of Search .............................. 604/68, 69, 70, 604/71, 72, 73, 131, 140, 141, 143, 145, 604/187

(56) References Cited

U.S. PATENT DOCUMENTS

| 4,089,334 A | * | 5/1978 | Schwebel et al. .............. 604/69 |
| 4,124,024 A | * | 11/1978 | Schwebel et al. .............. 604/69 |
| 6,328,714 B1 | * | 12/2001 | Bellhouse et al. .......... 604/232 |

* cited by examiner

Primary Examiner—Nicholas D. Lucchesi
Assistant Examiner—Mark K. Han
(74) Attorney, Agent, or Firm—Oliff & Berridge, PLC

(57) ABSTRACT

The technical field is that of pre-filled disposable needleless syringes, operating with a gas generator (100) and used for intradermal, subcutaneous and intramuscular injections of liquid active principle for therapeutic purposes in human and veterinary medicine. The inventive needleless syringe (1) is characterised in that it comprises a compact architecture body (2) and the gas generator (100) is released by a cap (17) covering said body (2), said cap (17) being adapted to slide along said body (2). Said releasing mode provides the syringe with great stability (1) at the time of injection.

17 Claims, 4 Drawing Sheets

NEEDLELESS SAFETY SYRINGE OF COMPACT ARCHITECTURE

The technical field of the invention is that of prefilled and disposable needleless syringes which function with a gas generator and which are used for intradermal, subcutaneous and intramuscular injections of liquid active principle for therapeutic use in human or veterinary medicine.

More particularly, the invention concerns a needleless syringe comprising a body, a gas generator, a chamber for expansion of said gases, a reservoir containing the active principle, and an injection system having at least one injection channel.

For the injection devices according to the invention, a liquid active principle is formed by a liquid of greater or lesser viscosity, or a liquid mixture, or a gel. The active principle can be a solid in solution in a solvent suitable for injection. It can also be a pulverulent solid in more or less concentrated suspension in a suitable liquid. The granulometry of the active principle must be compatible with the diameter of the conduits in order to avoid blockages.

In the whole of the text which follows, the expressions "compact form", "compact architecture" and "compact geometry" are equivalent expressions. They are attributed to syringes and signify that their height has a dimension of the same order of magnitude as that of their length while at the same time maintaining a minimum size. More quantitatively, the concept of "same order of magnitude" corresponds to a "height to length" ratio of between 0.5 and 2.5. In other words, neither of the aforementioned characteristics is really favoured over the other in terms of dimension, in contrast, for example, to the traditional syringes with needles, which are provided with a long slender body.

Needleless syringes of compact architecture have already been developed and are the subject of a number of patents. Reference may be made to U.S. Pat. No. 3,945,379 which relates to a needleless injection device having a compact geometry. Said device is in fact made up of two linear segments, approximately of the same length, and forming a right angle with one another. In this way, the entire drive part providing for the release of the gases is out of alignment with the part including the system for discharging the liquid active principle. The device is triggered by means of pressure on a button implanted in the side wall of the segment containing the gas reserve.

The patents U.S. Pat. No. 5,383,851, U.S. 5,399,163 and U.S. 5,520,639 describe a needleless hypodermic injection device which is also of compact architecture. This device is in the form of two linear segments, one representing the drive part of the device, the other providing for the expulsion of the active principle, and these two segments being parallel to one another and secured to one another head-to-tail. The device is triggered by depressing a button situated at one of the ends of the segment containing the gas reserve, said button having the function of puncturing a pressurized gas reserve.

Finally, EP 0,853,952 concerns a system of transdermal injection which is of compact form and is rechargeable. This injection system has an orifice into which it is possible to insert an independent firing casing which contains the liquid active principle. After use, this casing is removed from the system, then replaced by another casing ready for use. The generator involves an explosive substance which is initiated electrically by means of a battery.

The needleless syringes according to the invention are designed to meet a twin objective, which is to ensure injection in a direction perpendicular to the patient's skin while at the same time guaranteeing a high degree of safety of use by limiting the triggering possibilities exclusively to the configuration in which the part in contact with the skin and the triggering system are simultaneously subjected to a pressure applied by the user. The needleless syringes described in the prior art are of compact form but do not have any specific means in terms of shape, geometry or trigger system allowing them to meet the above two objectives.

The subject of the present invention is a needleless syringe comprising a body, a gas generator, a chamber for expansion of said gases, a reservoir containing the active principle, and an injection system having at least one injection channel, characterized in that the body has a compact architecture inducing the misalignment of the gas generator and of the reservoir containing the active principle, and the gas generator is triggered by a cap covering said body, said cap being able to slide along said body. In this way, the needleless syringes according to the invention have dimensions and a triggering method which allow them to be used with just one hand, providing for better control of the perpendicular hold and permitting greater stability of the syringe at the moment of injection. The triggering method, which is characterized in particular by a movement of translation of the cap along the axis of injection, also promotes this stability. The gas generator is preferably a pyrotechnic gas generator comprising a pyrotechnic charge and an initiation device.

The initiation system advantageously comprises a percussion device and a primer. It is also possible to use an initiation system based on a piezoelectric crystal or a roughening formed by two friction surfaces whose displacement creates a zone of inflammation.

The percussion device preferably includes a spring and a striker, said striker being in the form of a hollow cylindrical component which is provided at one of its ends with a projection and has, on its outer lateral surface, at least two lugs, each having an inwardly curved inclined plane, said striker enclosing said spring.

Advantageously, the hollow cylindrical component has, on its outer lateral surface, at least two protuberances of substantially parallelepipedal shape, said protuberances bearing against at least two limit stops on the body in order to prevent the striker from being translated under the action of the spring.

The cap preferably has, on the one hand, at least two locking stubs which bear against the protuberances of the striker in order to prevent said striker from undergoing a rotation about its axis, and, on the other hand, at least two overhangs which each end in an inwardly curved inclined plane, in such a way that the sliding of the cap along the body causes both the translation of the stubs, so as to free the striker in terms of rotation, and also the translation of said overhangs which come into contact with the lugs on the striker at the level of their respective inclined planes which engage each other, bringing about the rotation of said striker and the misalignment of the protuberances with the limit stops on the body. In more concrete terms, this type of percussion device functions in the following way: the striker which encloses a prestressed spring is locked in translation against at least one limit stop on the body. The sliding of the cap induces a rotation of the striker about its axis, by an angle which is sufficient to bring said striker and the limit stop on the body completely out of alignment. The striker, which is thus freed in translation, is flung abruptly toward the primer under the action of the spring which releases.

Such a percussion device could also be used in an initiation device involving a piezoelectric crystal.

The cap preferably has a means for securing it to the body, allowing it to remain in a position of maximum engagement. According to a preferred embodiment of the invention, the securing means consists of a tab which is elastically deformable and whose end is turned back to form a hook. In this way, the position of the cap engaged on the body appears instantly as a proof of use.

The gas generator advantageously constitutes a first linear subassembly of the body, and the reservoir containing the active principle and the injection system form a second linear subassembly of said body, the two subassemblies forming between them an angle of less than or equal to 90° and being connected to one another via the expansion chamber. This particular arrangement of the two subassemblies is dictated by the compact geometry of the syringe.

According to a preferred embodiment of the invention, the two subassemblies have mutually parallel axes and are connected to one another via the expansion chamber which has an axis perpendicular to the axes of said subassemblies.

In other words, the syringe, which comprises, in succession, the percussion device, the primer, the pyrotechnic charge, the expansion chamber, the reservoir containing the liquid active principle, and the injection system, has an overall U-shape. According to an alternative embodiment of the invention, the two linear subassemblies can be in contact with one another.

The cap is preferably able to slide along the body on an axis parallel to those of the two subassemblies. This sliding contributes to establishing the stability of the syringe at the moment of injection.

Advantageously, the ratio of the maximum height of said syringe to its maximum length is between 0.8 and 1.8, and preferably between 1.1 and 1.5. The height of the syringe is the dimension of said syringe measured on the axis of the two subassemblies, and the length is the dimension measured on an axis perpendicular to the axes of the two subassemblies and joining them. The height of the syringe is advantageously less than 8 cm.

A compression member is preferably arranged between the cap and the body in such a way as to push said cap back from said body. This member, which is preferably formed by a spring, induces a resistance intended to increase the force needed to push the cap down along the body.

The reservoir is advantageously formed by a tube obturated by an upstream piston plug and a downstream piston plug between which the active principle is contained. The tube is advantageously made of glass.

The two piston plugs are preferably made of a deformable material. They are obtained in particular by molding of elastomers which are compatible with the liquid active principle over a long period of time. These elastomers can be, for example, chlorobutyl or bromobutyl. The injection system preferably comprises an end component which has an internal recess and at least one peripheral injection channel, said recess being intended, during injection, to receive the downstream piston plug while leaving the injection channel clear.

In terms of functioning, the column of liquid is displaced until the downstream piston plug takes up a position in the internal recess. Once blocked in said recess, the piston plug deforms slightly in such a way as to free the entrance of the peripheral injection channel and allow the active principle to be expelled.

Advantageously, the cap completely covers the body and the injection system emerges from said cap.

The injection system and the cap preferably cooperate in order to trigger the syringe. The position of the cap relative to the body of the syringe will in fact determine the triggering of said syringe. Since, in a preferred manner, the injection system is integral with the body and comes into contact with the skin, it is by its agency that the sliding of the cap will take place. It is thus necessary to have a bearing surface in order to trigger the syringe.

The injection system advantageously ends in a retractable protective plate. Said plate preferably has substantially the same dimensions as the injection system and closely covers said system.

According to a preferred embodiment of the invention, the cap is continued by a stopper covering the injection system, said stopper having substantially the same cross section as that of the cap which it continues. In fact, the stopper and the retractable plate have the twin function of making the syringe safe by preventing any sliding of the cap along the body and thus any inadvertent triggering of said syringe, and of protecting the injection system against any undesired contamination prior to use. In a preferred manner, the stopper a) has a plane base,
b) is connected to the injection system via a system of bayonets,
c) obturates the cap by being in contact with it and in its continuity.

These structural characteristics mean that, before use, the syringe can be placed in stable equilibrium on a flat surface and will constitute an article which has a smooth contour and small size, and without any unwanted rough parts. The system of bayonets allows for simple unlocking of the syringe by rotating the stopper through 90° about the injection system.

The needleless syringes according to the invention have a triggering device conferring upon them a high degree of reliability and an improved level of safety. This is because such a device generates a pressure force profile which develops as a function of the depression of the cap, analogous to that shown in FIG. 5 and including three distinct phases. The first phase of this profile corresponds to a reversible course of the cap without triggering. It involves a depression of the cap during which the compression of the spring or of the blade situated between the cap and the body takes place. During this phase, relaxation of the pressure on the cap results in the immediate return of said cap to its initial position, brought about by the release of the spring or of the blade. The second phase relates to an irreversible course of the cap which guarantees triggering. More precisely, this phase commences when the complementary helical inclined planes of the cap and of the striker come into contact with one another, and it ends when said striker, after rotating sufficiently to be brought out of line with the limit stops on the body, is freed so as to strike the primer. In addition to the force which has to be applied to continue to contract the spring or the blade situated between the cap and the body, this second phase requires a supplementary force due to the resistance offered by the prestressed spring accommodated in the striker at the moment of causing the rotation of said striker. Finally, the third phase relates to a free course of the cap until it is locked, this course corresponding to the continuation of the compression of the spring or of the blade situated between the cap and the body. The force to be applied during this phase is in continuity with that to be applied during the first phase. This third phase ends when the cap has arrived at the end of its course and is maintained in this position by its locking member. Overall, such a force profile means that the syringe according to the invention cannot be triggered inadvertently or by accident and clearly shows that, on the contrary, it is necessary to perform a voluntary action in order to trigger it.

The needleless syringes according to the invention have the advantage of being in the form of a small compact object whose shape and dimensions allow it to be used easily and naturally with just one hand. Moreover, this compact form, unusual for an injection device, limits or even eliminates the apprehension which a patient may experience in the phase preceding injection, thereby increasing the effectiveness of treatment by permitting the latter to be carried through to completion. Finally, the needleless syringes according to the invention have the advantage of a high degree of safety based on means which are simple and functional, such as a self-locking stopper which can be easily unlocked, and particularly original, such as the percussion device which necessitates a gradual and specific force to trigger the syringe. This safety is heightened by the fact that the syringe can only be triggered in a very precise position of said syringe relative to the skin of the patient who is to be treated, and by the calibrated pressure force. The conjunction of this force and of this positioning perpendicular to the skin guarantees intimate contact of the injection system with the skin and prevents any risk of inadequate pressure upon injection.

A preferred embodiment of the invention is described in detail below with reference to FIGS. 1 to 5.

Figure 3A:
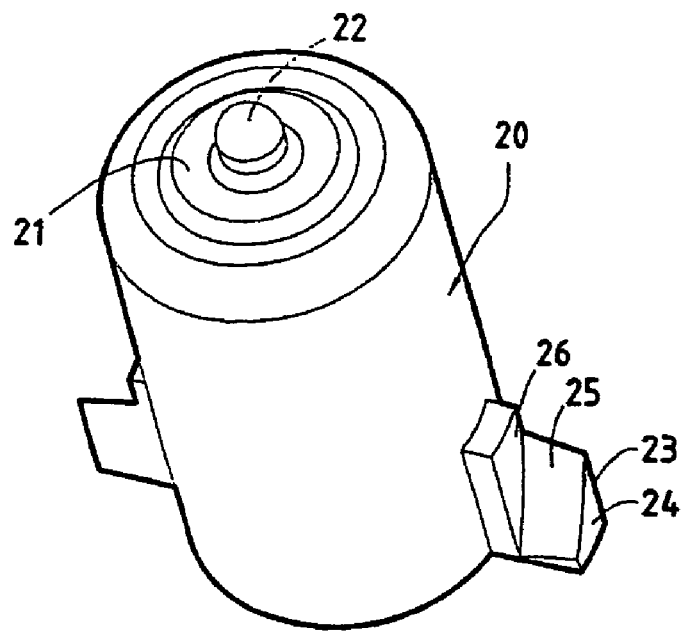
Figure 3B:
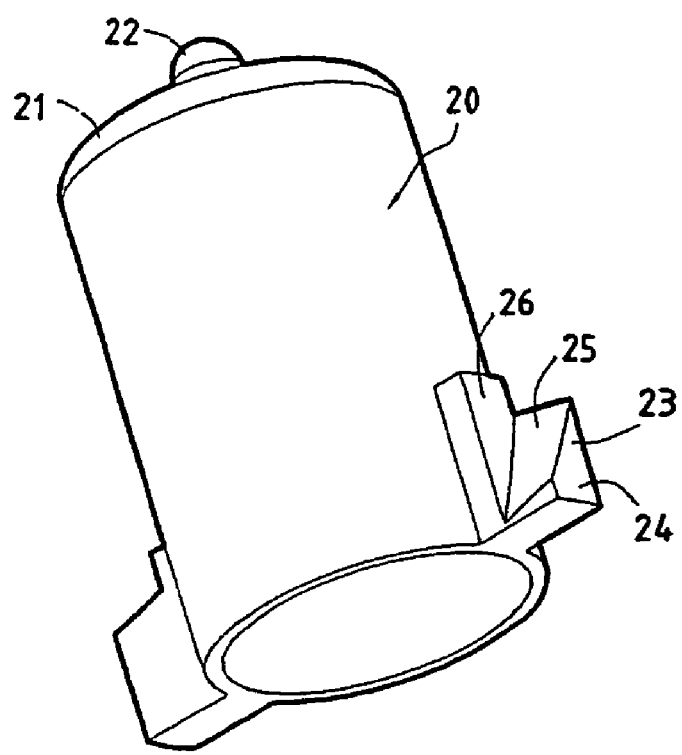

FIGS. 3a and 3b each show a perspective view of the striker of a needleless syringe according to the invention, the two views being shown each at a particular angle.

Figure 4:
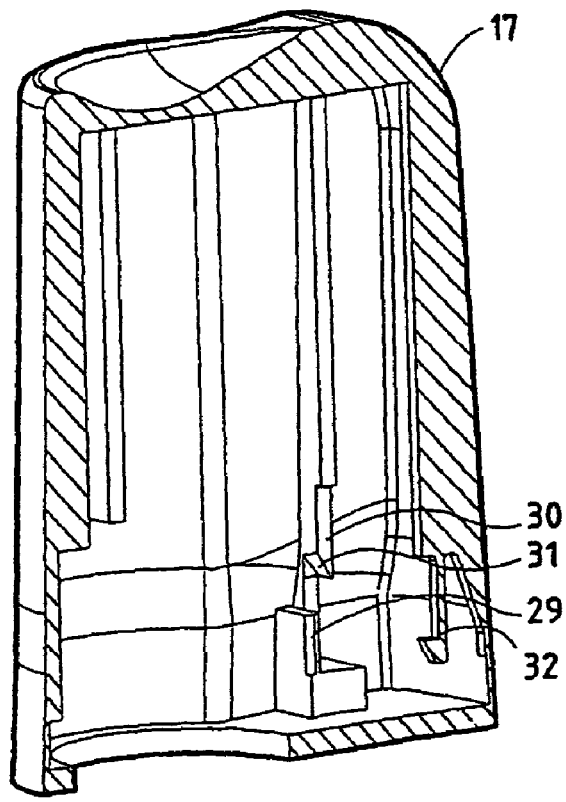

FIG. 4 is a perspective and cross-sectional view of the cap of a needleless syringe according to the invention, the section plane corresponding to its plane of symmetry.

Figure 5:
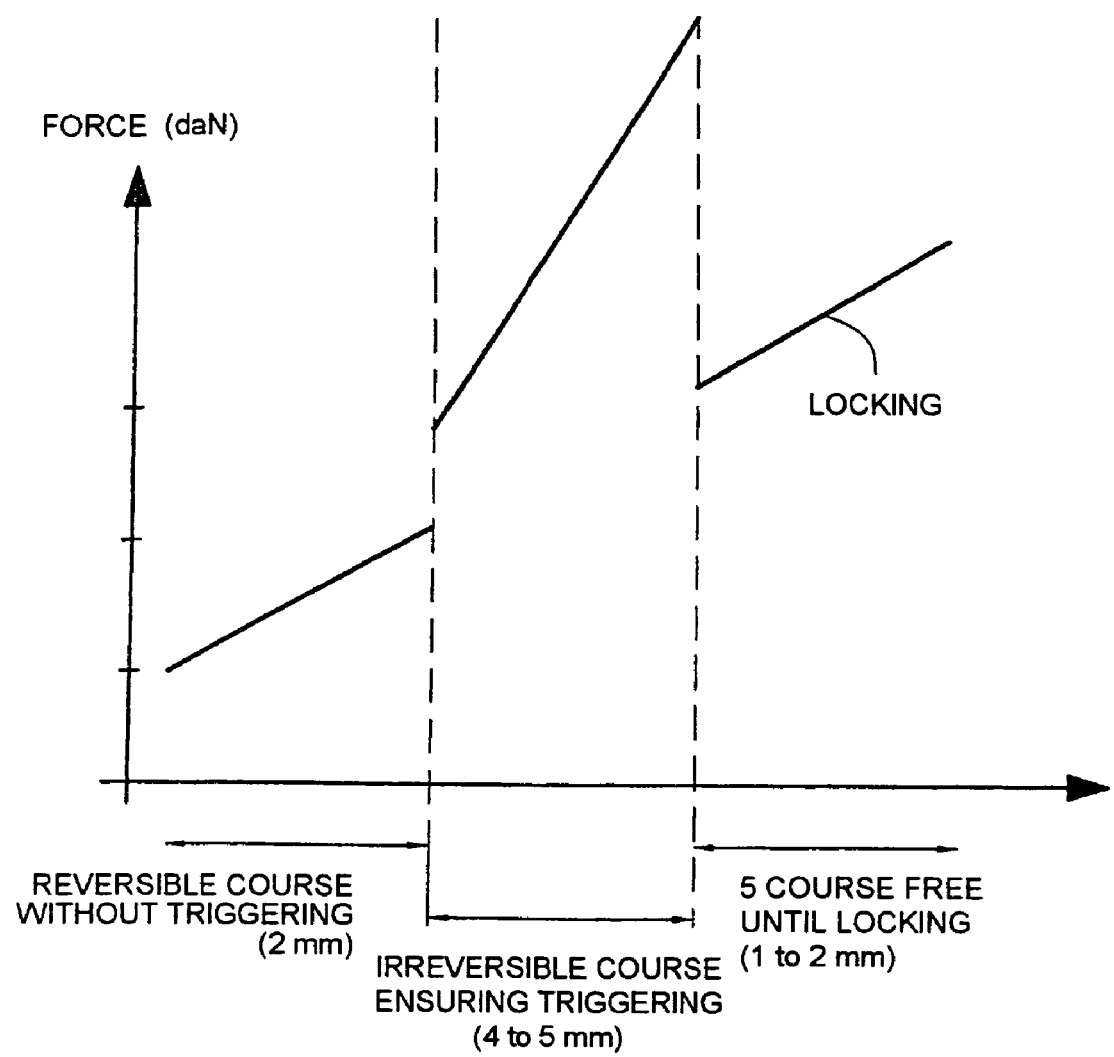

FIG. 5 is a graph showing the force to be applied to depress the cap as a function of the level of depression of said cap.

Figure 1:
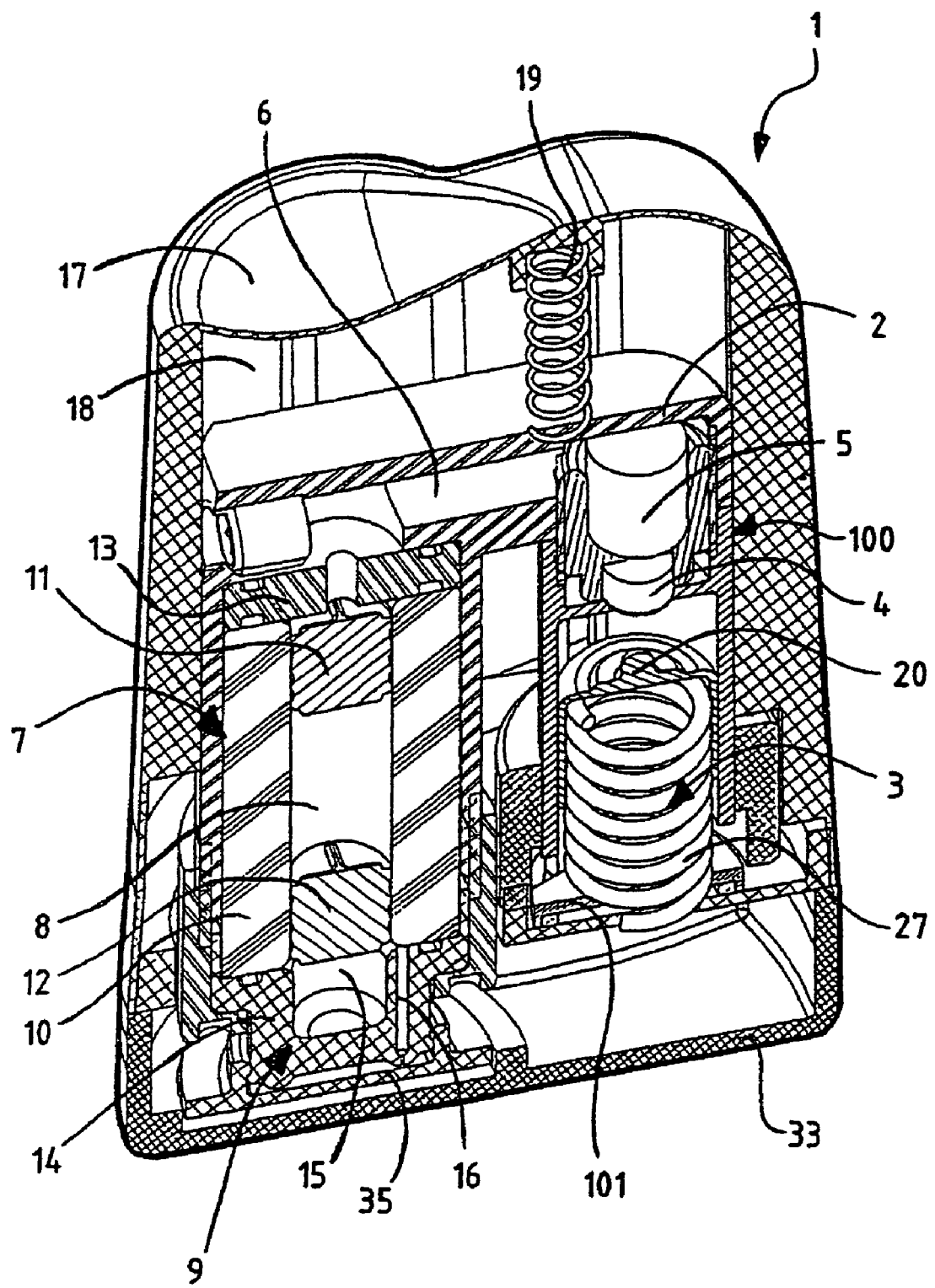
FIG. 1 is a longitudinal cross section through a needleless syringe according to the invention having a U-shaped body.

Referring to FIG. 1, a needleless syringe 1 according to the invention comprises a U-shaped body 2 comprising, in succession, a percussion device 3, a primer 4, a pyrotechnic charge 5, these three elements constituting a gas generator 100, an expansion chamber 6, a reservoir 7 containing the liquid active principle 8, and an injection system 9. The gas generator 100 constitutes a first linear subassembly of the body 2, and the reservoir 7 containing the active principle 8 and the injection system 9 form a second linear subassembly of said body 2, these two subassemblies having mutually parallel axes and being connected to one another via the expansion chamber 6 which has an axis perpendicular to the axes of said subassemblies. The reservoir 7 is formed by a glass tube 10 obturated by an upstream piston plug 11 and a downstream piston plug 12 between which the liquid active principle 8 is contained, said piston plugs being made of an elastomer-based deformable material. The reservoir 7 is inserted into the body 2 in such a way that its outer lateral wall is in contact with said body 2 and is fixed longitudinally, on the one hand, at its upstream part, by a cylindrical component 13 provided with a central opening permitting communication between the upstream piston plug 11 and the expansion chamber 6, said component 13 serving as a buffer between one of the ends of said reservoir 7 and the body 2, and, on the other hand, at its downstream part, by a hollow cylindrical component 14 obturated at one of its ends and having a flange at its other open end. This hollow cylindrical component 14 which constitutes the main component of the injection system 9 is fixed around the reservoir 7 like a hood, said reservoir 7 coming into abutment against the flange. Thus positioned, said hollow component 14 provides a free space forming an internal recess 15, said space having approximately the dimensions of the downstream piston plug 12 and being situated just behind the latter and in its continuity. The hollow cylindrical component 14 has, in its thickness, three peripheral injection channels 16 which are parallel to its axis and which open out, on the one hand, in the obturated face of said component 14 and, on the other hand, into the upper part of the recess 15 situated near the downstream piston plug 12. This hollow component 14 which constitutes the main part of the injection system 9 prevents the end of the glass tube 10 from coming directly into contact with the body 2.

A cap 17, provided with an opening, completely envelops the body 2. It is in the form of two identical half-shells which are attached to one another, and it is positioned about said body 2, in contact with the latter in the area of the outer lateral wall of its two subassemblies, and forming a space 18 between the segment of the body 2 formed by the expansion chamber 6 and the inner wall of the top of the cap 17 which is the closed part of said cap 17 situated remote from its opening. A helical spring 19 whose axis is parallel to that of the two subassemblies bears at its two ends against, on the one hand, the inner wall of the top of the cap 17 and, on the other hand, the body 2 at the level of the outer wall of the expansion chamber 6. Said spring 19 is stabilized laterally by two opposite stubs aligned with each other, one emerging from the inner face of the top of the cap 17, the other emerging from the outer face of the body 2 in the area of the expansion chamber 6. When the cap 17 is thus positioned about the body 2, the only thing emerging from its opening is a part of the hollow cylindrical component 14 of the injection system 9.

The gas generator 100 comprises three distinct and aligned parts:
- a percussion system 3 using a striker 20 and a prestressed spring 27 housed inside said striker 20,
- a conventional primer 4 of the sporting cartridge primer type,
- a pyrotechnic charge 5 consisting of a powder which is able to emit a large quantity of gas, for example a single powder based on nitrocellulose.

Referring to FIGS. 3a and 3b, the striker 20 is made up of a hollow cylindrical component which is open at one of its ends and is closed at its other end by a lid 21 of concave shape in relation to the body of said hollow cylindrical component, the top of said lid 21 ending in a rounded projection 22. The three constituent elements of the gas generator 100 are positioned in such a way that they are aligned with their axis of symmetry in coincidence, the percussion system 3 being the most upstream part of said generator 100, and the rounded projection 22 being the part of the striker 20 closest to the primer 4.

The striker 20 has, on its outer lateral surface, two diametrically opposed lugs 23 which are situated in the zone closest to its opening. Each of its lugs 23 has a plane top 24 having substantially the shape of a right-angled triangle of which one of the sides is parallel to the axis of the striker 20 and of which the other is perpendicular to said axis. Said lugs 23 have an inwardly curved inclined plane 25 which can be likened to a helical portion, the inclination of said plane 25 being defined by the segment joining the two sides of the triangular top 24, in other words by the hypotenuse of said triangle. The configuration of one lug 23 derives from that of the other lug by rotation of 180° about the axis of the striker 20. The striker 20 also has, on its outer lateral surface, two protuberances 26 of substantially parallelepipedal shape, with an edge parallel to the axis of said striker 20 and another edge perpendicular to said axis. Each protuberance 26 is situated between each lug 23 and the outer lateral wall of the striker 20. The spring 27 which is housed in the striker 20 is prestressed and bears on a plate 101 for closing the base of the generator 100, said plate 101 being situated remote from the projection 22 in relation to the striker 20.

Referring to FIG. 1, the striker 20 is positioned in the generator 100 in such a way that it bears against two limit stops of said generator 100, in the area of its two protuberances 26, and, more precisely, in the area of the upper edge of each of the two protuberances 26, said edge being perpendicular to the axis of the striker 20. Referring to FIG. 4, the cap 17 has, on its inner face, two flat stubs 29 each placed on a half-shell, in a position symmetrical to one another, said stubs 29 bearing against the protuberances 26 of the striker 20 and, more precisely, against one of the two edges of the protuberances 26 which is parallel to the axis of said striker 20.

The cap 17 also has two overhangs 30 which each end in an inwardly curved inclined plane 31 which can be likened to a helical portion. Said overhangs 30 are placed in line with the lugs 23 of the striker 20 so that the inclined planes 25 of the lugs 23 of the striker 20 are facing the inclined planes 31 of the overhangs 30 of the cap 17 and in complementary positions. In other words, if the inclined planes 31 ending the overhangs 30 of the cap 17 were to be brought into contact with the inclined planes 25 of the lugs 23 of the striker 20 by simple translation, they would engage perfectly with one another. The cap 17 has a tab 32 which is elastically deformable and whose end is turned back to form a hook. This is a securing device which, when the cap 17 has slid along the body 2, allows said cap to remain in its final position corresponding to maximum engagement.

Figure 2:
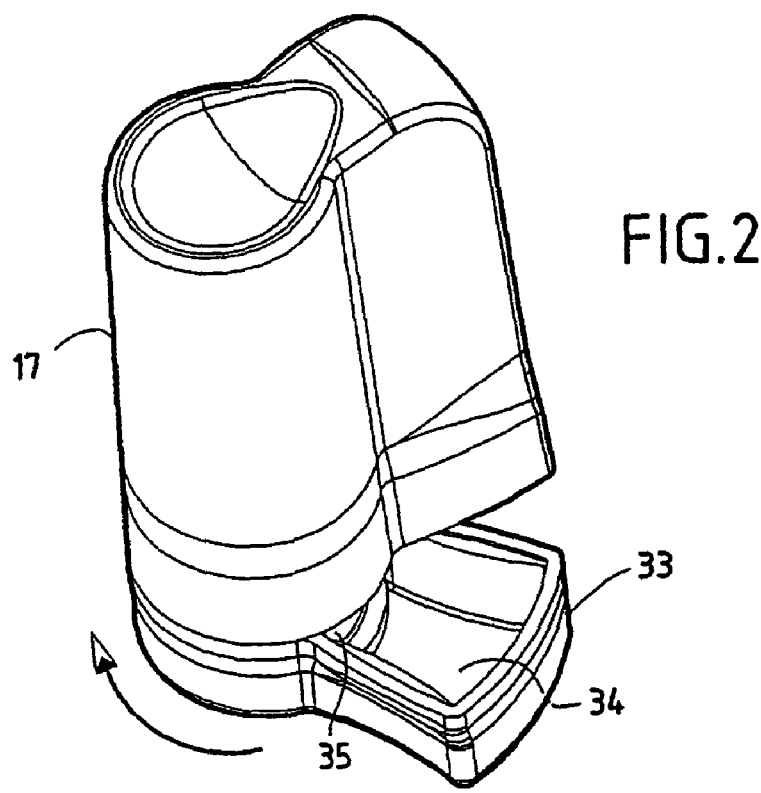
FIG. 2 is a perspective view of a needleless syringe according to the invention showing the position of the stopper in relation to the cap.

Referring to FIG. 2, a needleless syringe 1 according to the invention has a closure stopper 33 with a plane base 34 and substantially the same cross section as that formed by the opening of the cap 17. Thus, equipped with its stopper 33, the syringe 1 is in the form of a smooth and homogeneous object which does not exhibit any roughness or any breaks in its relief. The stopper 33 is fixed to the syringe 1 in the area of the part of the hollow cylindrical component 14 of the injection system 9 emerging from the cap 17. More precisely, the stopper 33 has, on its base 34, a small hood 35 which is fixed about the end of said hollow component 14 emerging from the cap 17 via a system of bayonets. By means of a simple 90° rotation it is possible to remove said stopper 33 which protects said system 9 by virtue of its hood 35 and prevents any sliding of the cap 17 along the body 2.

The mode of functioning of a needleless syringe 1 according to the invention is as follows:

The user unlocks the syringe 1 by removing the stopper 33 by turning it through 90°, as is indicated by the arrow in FIG. 2. He places the injection system 9 against the skin of the patient who is to be treated and, by pressing with a finger, depresses the cap 17 which slides along the body 2 until the inwardly curved inclined planes 31 of the overhangs 30 of said cap 17 come into contact with the inwardly curved inclined planes 25 of the striker 20 facing them. During this first phase, it has been necessary to apply a moderate pressure just to compress the spring 19 situated between the body 2 and the cap 17. By continuing to apply pressure on the cap 17, the stubs 29 which were in contact with the protuberances 26 of the striker 20 translate until they are no longer in contact with said protuberances 26, thus freeing the striker 20 in terms of rotation. Simultaneously, the overhangs 30 bear on the lugs 23 of the striker 20 and, by virtue of the inwardly curved inclined planes 25, 31 which cooperate, bring about the rotation of said striker 20. The amplitude of this rotation is such that it brings about the misalignment of the limit stops of the generator 100 and the protuberances 26 of the striker 20 which, as it is no longer locked, is accelerated so that its projection 22 impacts the primer 4 under the action of the release of the spring 27 which it encloses. During this phase, the forces to be applied have increased because it has been necessary to overcome, during rotation of the striker 20, the resistance offered by the prestressed spring 27 accommodated in said striker 20. The initiation of the primer 4 fires the pyrotechnic charge 5 which decomposes by combustion to supply gases. The gases invade the expansion chamber 6 and, when the pressure is sufficient, they exert a thrust on the column of liquid formed by the two piston plugs 11, 12 and the liquid active principle 8. The downstream piston plug 12 completely occupies the internal recess 15, allowing the liquid active principle 8 to empty into the peripheral injection channels 16. As the thrust continues to be exerted on the upstream piston plug 11, the liquid active principle 8 is then expelled through the channels 16 until the upstream piston plug 11 comes into contact with the downstream piston plug 12.

Just after the striker 20 impacts the primer 4 in order to trigger the syringe 1, the cap 17 continues to be driven down, without any marked effort, in a continuity of the movement, and it stops moving when the spring 19 situated between said cap 17 and the body 2 is compressed to the maximum extent. During the sliding of the cap 17 along the body 2, the tab 32 has slid along the body 2 and deformed elastically in order to comply with the relief of said body 2 and it has finally fastened on the shoulder of the body 2 via its turned-back end. After use, the cap 17 thus remains in the depressed position.

What is claimed is:

1. A needleless syringe comprising a body, a gas generator, a chamber for expansion of said gases, a reservoir containing the active principle, and an injection system having at least one injection channel, characterized in that the body has a compact architecture inducing the misalignment of the gas generator and of the reservoir containing the active principle, and the gas generator is triggered by a cap which covers said body, said cap being able to slide along said body.

2. The needleless syringe as claimed in claim 1, characterized in that the gas generator is a pyrotechnic gas generator comprising a pyrotechnic charge and an initiation device.

3. The needleless syringe as claimed in claim 1, characterized in that, on the one hand, the gas generator constitutes a first linear subassembly of the body, and, on the other hand, the reservoir containing the active principle and the injection system form a second linear subassembly of said body, the two subassemblies forming between them an angle of less than or equal to 90° and being connected to one another via the expansion chamber.

4. The needleless syringe as claimed in claim 3, characterized in that the two subassemblies have mutually parallel axes and are connected to one another via the expansion chamber which has an axis perpendicular to the axes of said subassemblies.

5. The needleless syringe as claimed in claim 4, characterized in that the cap is able to slide along the body on an axis parallel to those of the two subassemblies.

6. The needleless syringe as claimed in claim 1, characterized in that the ratio of the maximum height of said syringe to its maximum length is between 0.8 and 1.8.

7. The needleless syringe as claimed in claim 1, characterized in that a compression member is arranged between the cap and the body in such a way as to push said cap back from said body.

8. The needleless syringe as claimed in claim 1, characterized in that the reservoir is formed by a tube obturated by an upstream piston plug and a downstream piston plug between which the active principle is contained.

9. The needleless syringe as claimed in claim 1, characterized in that the cap completely covers the body and the injection system emerges from said cap.

10. The needleless syringe as claimed in claim 1, characterized in that the injection system and the cap cooperate in order to trigger said syringe.

11. The needleless syringe as claimed in claim 1, characterized in that the cap is continued by a stopper covering the injection system, said stopper having substantially the same cross section as that of the cap which it continues.

12. The needleless syringe as claimed in claim 1, characterized in that the cap has a means for securing it to the body, allowing it to remain in a position of maximum engagement.

13. A needleless syringe comprising a body, a gas generator, a chamber for expansion of said gases, a reservoir containing the active principle, and an injection system having at least one injection channel, characterized in that the body has a compact architecture inducing the misalignment of the gas generator and of the reservoir containing the active principle, and the gas generator is triggered by a cap which covers said body, said cap being able to slide along said body, characterized in that the injection system ends in a retractable protective plate.

14. A needleless syringe comprising a body, a gas generator, a chamber for expansion of said gases, a reservoir containing the active principle, and an injection system having at least one injection channel, characterized in that the body has a compact architecture inducing the misalignment of the gas generator and of the reservoir containing the active principle, and the gas generator is triggered by a cap which covers said body, said cap being able to slide along said body, characterized in that the cap (is continued by a stopper covering the injection system, said stopper having substantially the same cross section as that of the cap which it continues, and the stopper a) has a plane base, b) is connected to the injection system via a system of bayonets, and c) obturates the cap by being in contact with it and in its continuity.

15. A needleless syringe comprising a body, a gas generator, a chamber for expansion of said gases, a reservoir containing the active principle, and an injection system having at least one injection channel, characterized in that the body has a compact architecture inducing the misalignment of the gas generator and of the reservoir containing the active principle, and the gas generator is triggered by a cap which covers said body, said cap being able to slide along said body, characterized in that the gas generator is a pyrotechnic gas generator comprising a pyrotechnic charge and an initiation device, the initiation device comprises a primer and a percussion device which includes a spring and a striker, said striker being in the form of a hollow cylindrical component which is provided at one of its ends with a projection and has, on its outer lateral surface, at least two lugs, each having an inwardly curved inclined plane, said striker enclosing said spring.

16. The needleless syringe as claimed in claim 15, characterized in that the hollow cylindrical component has, on its outer lateral surface, at least two protuberances of substantially parallelepipedal shape, said protuberances bearing against at least two limit stops on the body in order to prevent the striker from being translated under the action of the spring.

17. The needleless syringe as claimed in claim 16, characterized in that the cap has, on the one hand, at least two locking stubs which bear against the protuberances of the striker in order to prevent said striker from undergoing a rotation about its axis, and, on the other hand, at least two overhangs which each end in an inwardly curved inclined plane, in such a way that the sliding of the cap along the body causes both the translation of the stubs, so as to free the striker in terms of rotation, and also the translation of said overhangs which come into contact with the lugs on the striker at the level of their respective inclined planes which engage each other, bringing about the rotation of said striker and the misalignment of the protuberances with the limit stops on the body.

* * * * *